US006350737B1

(12) United States Patent
Zak et al.

(10) Patent No.: US 6,350,737 B1
(45) Date of Patent: Feb. 26, 2002

(54) PLATINUM COMPLEX, ITS PREPARATION AND THERAPEUTIC APPLICATION

(75) Inventors: Frantisek Zak, Brno; Adolf Mistr, Tisnov; Anna Poulova, Ivancice; Milan Melka, Hradec Kralove; Jaroslav Turanek, Jemnice; Dana Zaluska, Dolni Loucky, all of (CZ)

(73) Assignee: Pliva-Lachema, A.S., Brno (CZ)

( * ) Notice: Subject to any disclaimer, the term of this patent is extended or adjusted under 35 U.S.C. 154(b) by 0 days.

(21) Appl. No.: 09/700,513

(22) PCT Filed: May 24, 1999

(86) PCT No.: PCT/CZ99/00014

§ 371 Date: Jan. 29, 2001

§ 102(e) Date: Jan. 29, 2001

(87) PCT Pub. No.: WO99/61450

PCT Pub. Date: Dec. 2, 1999

(30) Foreign Application Priority Data

May 27, 1998 (CS) .......................... PV 1627-98

(51) Int. Cl.[7] .................. A61K 47/40; A61K 33/24; C08B 37/16
(52) U.S. Cl. .................. 514/58; 514/492; 536/103; 556/137
(58) Field of Search ............... 556/137; 514/58, 514/492; 536/103

(56) References Cited

U.S. PATENT DOCUMENTS 5,225,207 A * 7/1993 Barreau et al. .......... 424/649

OTHER PUBLICATIONS

CA:119–84501 abs of Inorg Chem 32(12) pp 2717–23 by Rochon et al, 1993.*
CA:115:63438 abs of EP3893338, Sep. 1990.*
CA:83:141759 abs of Chem–Biol Interact. 11(3) pp 145–161 by Braddock et al, 1975.*
CA:110:375 abs of Khim.–Farm. Zh. 22(7) pp 808–810 by Stetsenko, 1988.*

* cited by examiner

Primary Examiner—Jean F. Vollano
(74) Attorney, Agent, or Firm—Notaro & Michalos P.C.

(57) ABSTRACT

A platinum complex of the general formula (I) wherein X represents a halogen atom and A represents a group —$NH_2$—R wherein R is a tricyclic hydrocarbon moiety containing 10 to 14 carbon atoms which may be optionally substituted on the tricyclic ring by one or two alkyl group(s) containing 1 to 4 carbon atoms, and, furthermore, an inclusion complex of the above platinum complex with beta- or gamma-cyclodextrin which may be optionally substituted by a hydroxyalkyl group of 1 to 6 carbon atoms. There are also disclosed a method for the preparation of the complex of the formula (I) based on bringing into reaction a solution of an akaline metal salt of amminetrihalogenoplatinate (1–) in a polar organic solvent or in water with a primary amine of formula R—$NH_2$, wherein R is a tricyclic hydrogen moiety containing 10 to 14 carbon atoms, which may be optionally substituted on the tricyclic ring by one or two alkyl group(s) each containing 1 to 4 carbon atoms, at the temperature in the range of 0 to 100° C., as well as a method for manufacture of the above inclusion complex. The both disclosed complexes may be used as such or as a part of pharmaceutical composition in a therapy of oncologic diseases.

8 Claims, 1 Drawing Sheet

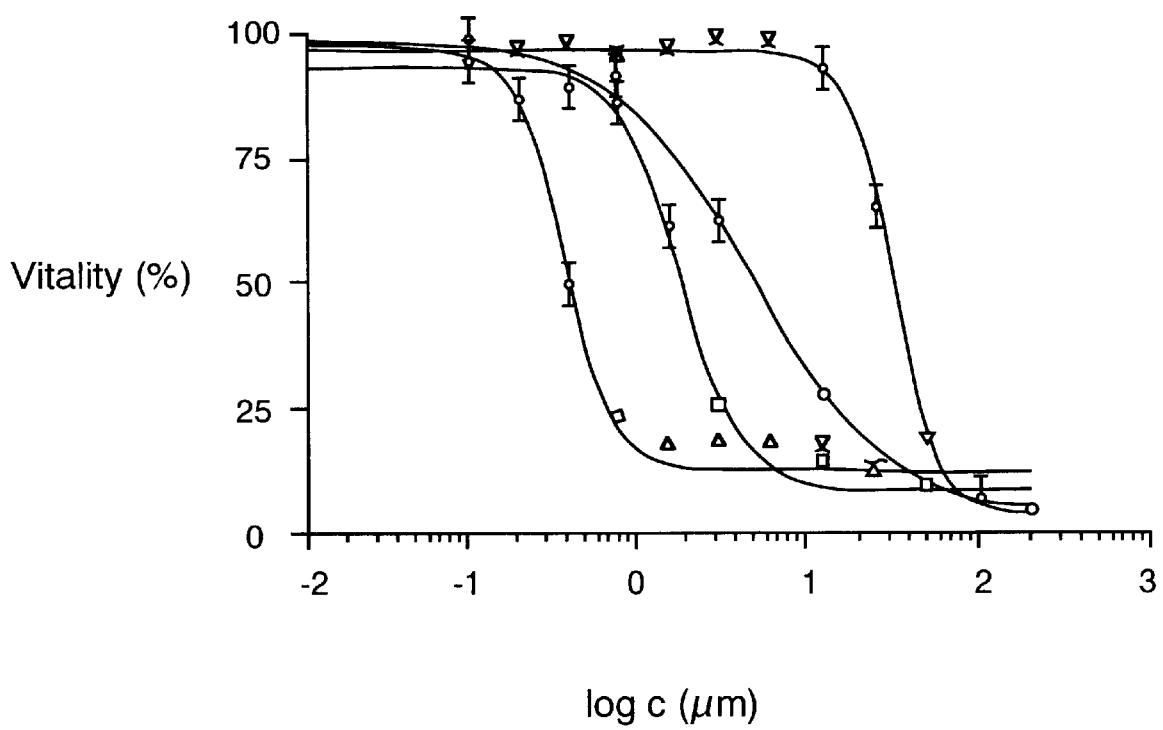

PLATINUM COMPLEX, ITS PREPARATION AND THERAPEUTIC APPLICATION

This is the national phase of PCT/CZ99/00014, filed May 24, 1999, now WO 96/61450.

FIELD OF THE INVENTION

The invention deals with a new platinum complex of oxidation number II which is useful in medicinal practice for a therapy of oncological diseases. The invention further discloses use of the complex as a pharmaceutical and pharmaceutical compositions containing that platinum complex as the active substance.

BACKGROUND OF THE INVENTION

Platinum complexes effective as cytostatic agents were introduced into medicinal practice by the end of seventieths of this century. The first pharmaceutical product of this type was cisplatin (cis-diammine-dichloroplatinum(II) complex). During further development, tens of platinum complexes were synthetised and tested; among them, carboplatin (cis-diammine-/1,1-cyclobutanedicarboxylato/platinum(II) complex) attained the biggest importance in oncology. Further, there were described assymetric complexes of platinum in which one ammino-ligand has been replaced by an alkylamine group (U.S. Pat. No. 4,329,299).

At present, platinum complexes which would express higher antitumor efficiacy and lower side effects in comparison with known platinum complexes are still being searched.

Now, within the present invention, certain new platinum complexes which possess higher antitumor efficiacy in comparison with platinum complexes of the prior art and lower undesired side effects in comparison with cited known complexes were found. These new complexes represent the principle of the present invention.

SUMMARY OF THE INVENTION

The first aspect of the present invention is a platinum complex with oxidation number II of formula (I)

(I)

wherein

X represents a halogen atom, and

A represents a primary tricyclic amine containing 10 to 14 carbon atoms, which may be optionally substituted on the tricyclic ring by one or two alkyl group(s) each containing 1 to 4 carbon atoms, and, furthermore, an inclusion complex of the above platinum complex with beta- or gamma-cyclodextrin which may be optionally substituted by hydroxyalkyl groups containing 1 to 6 carbon atoms.

Especially advantageous complex of the present invention is a platinum complex of formula (I) wherein A represents an adamantylamino group and X has the above defined meaning. Furthermore, another advantageous platinum complex of the present invention is a complex of formula (I) wherein A represents a 3,5-dimethyladamantylamino group and X has the above defined meaning.

Another aspect of the present invention is a process for the preparation of the platinum complex of the formula (I) which is characterized in that a solution of an alkali metal salt of amminetrihalogenoplatinate (1−) in a polar organic solvent or in water is subjected to a reaction. with a primary amine of formula $NH_2$—R, wherein R is a tricyclic hydrogen moiety containing 10 to 14 carbon atoms which may be optionally substituted on the tricyclic ring by one or two alkyl groups of one to four carbon atoms, at the temperature of 0 to 100° C.

The invention also provides a process for the preparation of an inclusion complex of the platinum complex of formula (I) with beta- or gamma-cyclodextrin which may be optionally substituted by hydroxyalkyl groups containing 1 to 6 carbon atoms said process being characterized in that solution of the platinum complex of formula (I) in an organic solvent is mixed with an aqueous solution of beta- or gamma-cyclodextrin which is optionally substituted by hydroxyalkyl groups containing 1 to 6 carbon atoms, and, in the following step, the solvents are evaporated from the obtained solution.

Still another aspect of the invention is the platinum complex of formula (I) above or its inclusion complex with beta- or gamma-cyclodextrin for use as a pharmaceutical.

The next aspect of the invention provides a pharmaceutical composition for therapy of oncological diseases, characterized in that it contains, as the active substance thereof, at least one platinum complex of above formula (I) or its inclusion complex with beta- or gamma-cyclodextrin, and at least one pharmaceutical excipient.

Moreover, the platinum complexes of formula (I) may be further used as starting substances for production of analogically substituted platinum complexes with oxidation number IV which are useful for peroral application.

The platinum complexes of the present invention are novel chemical compounds as until now neither these compounds have been specifically disclosed in any document of the prior art nor their properties have been characterized herein nor a method of their production has been disclosed. The utility of these compounds as active substances in the therapy of oncological diseases is likewise novel and inventive as it was not possible to deduce from the prior art by an obvious way that the presence of primary tricyclic amine ligand in divalent platinum complexes would lead to a substantial increase of antitumor activity of the novel compounds of the present invention.

In further part, the invention will be described in more detail by means of examples of concrete embodiment. It must be understood that these examples are disclosed for illustrative purposes and that they by no means limit the scope of the invention which is rather defined by the patent claims.

BRIEF DESCRIPTION OF THE DRAWINGS

FIG. 1 is a graphic representation of inhibition curves of the invention and comparative compounds.

Synthesis of cis-(1-adamantylamine) amminedichloroplatinum (II) (hereinafter coded as "LA-9")

A solution of 19.55 g (54.6 mmol) of potassium amminetrichloroplatinate (1−) in 84 ml of water was filtered and a mixture of 84 ml of water and 45.4 g (273.4 mmol) of potassium iodide was added to the filtrate. To the mixture, 8.27 g (54.6 mmol) of 1-adamantylamine was added under nitrogen atmosphere. The resulted mixture was stirred under exclusion of air and light at room temperature for 22 hours. The resulted precipitate was filtered off under nitrogen and washed with water free from dissolved gases. After drying in vacuum dryer, an intermediate containing 3.09% of chlorine and 33.03% of iodine was obtained. This intermediate was suspended in 170 ml of water and 17.75 g (104.5 mmol) of silver nitrate (90% of theoretical amount based on the content of halogenides in the intermediate) was added to the suspension. After stirring for 70 hours at room temperature under exclusion of light and air, the undissolved part was filtered and washed with small amount of water. Concentrated hydrochloric acid (19 ml, 205 mol) was slowly added to the filtrate and the mixture was stirred under exclusion of air and light at room temperature for 20 hours. Solid crude product was filtered off and washed subsequently by 0.1M hydrochloric acid, ethanol and ether. After drying in a vacuum oven, 16.46 g of the crude product was obtained (68%, based on the starting potassium amminetrichloroplatinate (1−)).

The crude product (16.36 g, 37.7 mmol) was dissolved in 200 ml of dimethylformamide, the obtained solution was filtered and, under cooling, 600 ml of 0.1M hydrochloric acid was added to the filtrate. The resulted solid precipitate was filtered off, washed subsequently by 0.1M hydrochloric acid, ethanol and ether and dried in vacuum dryer. The yield was 14.70 g of the desired product (89.8% of theory, based on the starting crude product).

Identity of the obtained product was confirmed by IR and 1H NMR spectral analysis. Crystal and molecular structure of the obtained platinum complex was tested on a prepared single crystal by x-ray structure analysis, whereby the results of spectral methods were confirmed. Purity of the obtained product was determined by high performance liquid chromatography.

Elemental analysis of the product for $C_{10}H_{20}Cl_2N_2Pt$:

|  | C (%) | H (%) | N (%) | Cl (%) |
|---|---|---|---|---|
| found | 27.75 | 4.55 | 6.37 | 16.25 |
| calculated | 27.66 | 4.64 | 6.45 | 16.33 |

EXAMPLE 2

Synthesis of cis-(1-amino-3,5-dimethyladamantane) amminedichloroplatinum (II) complex (hereinafter will be called as "LA-13")

1-Amino-3,5-dimethyladamantane (8.06 m, 42 mmol) was added to a freshly filtered solution of 13.95 g (39 mmol) of potassium amminetrichloroplatinate (1−) under stirring, at room temperature and under nitrogen atmosphere. The resulted mixture was stirred for 15 hours at 50° C. under protection against light and air. After cooling to room temperature, the resulted solid precipitate was filtered under nitrogen blanket and washed with n-hexane. The filter cake was dried by passing air stream through the funnel and the dried raw product was dissolved in 120 ml of dimethylformamide. The filtrate was mixed with 360 ml of 0.1M hydrochloric acid. The resulted precipitate was filtered off and washed with 0.1M hydrochloric acid and ether. After drying in vacuum, oven, 6.25 g of the desired product was obtained (34.6% of the theoretical yield, based on starting potassium amminetrichloroplatinate (1−).

Identity of the obtained product was confirmed by IR spectral analysis while its purity was determined by high performance liquid chromatography.

Elemental analysis of the product for $C_{12}H_{24}Cl_2N_2Pt$:

|  | C (%) | H (%) | N (%) | Cl (%) |
|---|---|---|---|---|
| found | 31.59 | 5.37 | 5.98 | 15.53 |
| calculated | 31.18 | 5.23 | 6.06 | 15.34 |

EXAMPLE 3

Synthesis of inclusion complex of the compound LA-9 with hydroxypropyl-beta-cyclodextrin (hereinafter will be called as "inclusion drug form of LA-9")

The compound LA-9 was dissolved in dimethylformamide to obtain a solution with final concentration of 25 g/l. Hydroxypropyl-beta-cyclodextrin was added to the solution in such amount which was necessary to obtain molar ratio LA-9/cyclodextrin 1:3. Buffered aqueous phase of 10 mM Hepes of pH 7.3 was added to the solution of LA-9 and cyclodextrin under stirring and at room temperature until final volume ratio of dimethylformamide and aqueous phase was 1:10. The undissolved cyclodextrin dissolves rapidly even after first additions of the aqueous phase. Dimethylformamide and water were removed from the solution of the inclusion complex by lyophilisation.

Cytostatic activity of compounds of the present invention has been tested in vitro on tumor lines. The MTT test was chosen for screening the effectivity of the respective compounds. The test is based on reaction of a tetrazolium salt with respirating mitochondria of living cells. The resulted insoluble formazan is solubilized and its amount is determined on a microplate reader. This method is being used as a standard one for evaluation of cytostatic effect of pharmaceutically active compounds (Tim Mosmann, Rapid colorimetric assay for cellular growth and survival, Application to proliferation and cytotoxicity assays, Journal of Immunological Methods, 65 (1983), 55–63). Inhibition constant (IC50) represents such a concentration of a substance which causes 50% supression of growth of a cell culture. This constant has been determined from a graph of dependence of MTT value (mitochondrial activity of cells) on the concentration of tested substance. A GraphPad Prism programme was used for determination of the constant from the measured values, whereby Boltzman sigmoid was used for constructing a curve from single experimental points. Chosen cell lines are standard lines used for routine screening of cytostatic effect of pharmacologically active compounds.

EXAMPLE 4

Antitumor Activity on Mice Tumor Lines

Within this example, lines P 815 (mastocytoma) and L 1210 (lymphocyte leucaernia line) were tested. The effect of LA-9 was compared to that of carboplatin by MTT test.

The found values of IC50 were 1.1 μM for the P-815 line and 1.5 μM for the L-1210 line. To the contrary, carboplatin (both in a free form or as a complex with cyclodextrin) exhibited the IC50 value of 105 μM, i.e. it was approximately hundred times less active than LA-9.

EXAMPLE 5

Antitumor Activity on Human Tumor Cells

Comparation experiments were performed on lymfoblastic leucaemia line CEMt. The MTT test was used for evaluation of cytotoxic effect. Inhibition constant IC50 was determined for compounds LA-9 (IC50=0.36 μM, Cisplatin (IC50=1.9 μM), Carboplatin (IC50=30.4 μM) and Oxaliplatin (IC50=4.8 μM).

Graphic expression of courses of inhibition curves is given on FIG. 1. The points on curves are marked as follows: for LA-9=upwards orientated triangle, for Carboplatin= downwards orientated triangle, for Cisplatin=square, for Oxaliplatin=circle. Vitality of cells was determined by a standard spectrophotometric MTT test based on reduction of 3-(4,5-dimethylthiazol-2-yl)-2,5-diphenyltetrazolium bromide by vital cells under formation of a formazane.

Ocular melanoma VUP (Masaryk Oncological Institute, Brno) exhibited approximately ten times higher sensibility towards LA-9 (IC50=9 μM) in comparison with Carboplatin (IC50=95 μM).

EXAMPLE 6

Antitumor Activity in vivo

Antitumor activity of the compound LA-9 and cisplatin has been compared on animals with solid mammal adenocarcinoma MC 2111 after single dose intravenous application at 5$^{th}$ day after inoculation of tumor cells. This way of administration which is characteristic for platinum complexes was possible by a preparation of soluble application form.

Mice female DBA/1 of body mass 22.9–25.8 g were used in this experiment. Tumors were developed by s.c. inoculation of 0.2 ml of a tumor homogenate diluted in 1:1 volume ratio with an isotonic glucose solution. Tested compounds were applied in a form of an isotonic water solution prepared immediately before application by dissolution of corresponding lyophilised product in water for injections and further by dilution with isotonic sodium chloride solution ad hoc according to the need, in volumes of 0.1–0.4 ml per 20 g of body mass of an animal, as apparent from the following table.

TABLE

| Compound | Dosage of the substance (mg/kg) | n(j) | Median of survival time (days) | Survivors (% of control) | LTS |
|---|---|---|---|---|---|
| Control | 0 | 8 | 26.0 | 100 | 0 |
| Platidiam | 4 | 8 | >76.5 | >294 | 4 |
|  | 2 | 8 | 39.5 | 152 | 2 |
|  | 1 | 8 | 28.5 | 110 | 2 |

TABLE-continued

| Compound | Dosage of the substance (mg/kg) | n(j) | Median of survival time (days) | Survivors (% of control) | LTS |
|---|---|---|---|---|---|
| Inclusion drug form of LA-9 | 24 | 8 | 29.0 | 112 | 3 |
|  | 12 | 8 | >106.5 | >410 | 4 |
|  | 6 | 8 | >92.5 | >356 | 4 |

The compound LA-9 increased the median of survival time at a dose of 12 mg/kg to 410% in comparison with the control group, whereby the distribution of single survival times differed statistically significantly at significance level α=0.05 when evaluated by non-parametric test according to Hajek (Fabian V., Zakladni statisticke metody [Basic methods of statistics], NCSAV Prague 1963). Half of the animals survived in permanent complete remission and were destroyed after termination of the experiment without macroscopic manifestation of a tumor. Positive influence on survival, though statistically insignificant, can be regarded as sufficient proof of antitumor activity and low toxicity of the tested compound.

Low toxicity of LA-9 can be also demonstrated by evaluation of the coefficient of body weight gain. The administration of LA-9 has been accompanied with less than 10% loss of body weight. Optimum dosage of LA-9 has been 13–16 mg/kg for animals used in the tests. The value of maximum tolerable dose (MDT) can be estimated at around 25 mg/kg.

What is claimed is:
1. A platinum complex with oxidation number II of formula (I)

(I)

wherein
  X represents a halogen atom,
  A represents a group —NH$_2$—R, wherein R is tricyclic hydrocarbon moiety containing 10 to 14 carbon atoms, which may be optionally substituted on the tricyclic ring by one or two alkyl group(s) of 1 to 4 carbon atoms.
2. An inclusion complex of a platinum complex with oxidation number II of formula (I)

(I)

wherein
  X represents a halogen atom,
  A represents a group —NH$_2$—R, wherein R is a tricyclic hydrocarbon moiety containing 10 to 14 carbons atoms, which may be optionally substituted on the tricyclic ring by one or two alkyl group(s) of 1 to 4 carbon atoms, with beta- or gamma-cyclodextrin which may be optionally submitted by a hydroxyalkyl group of 1 to 6 carbon atoms.

3. A platinum complex according to claim 1 of the formula (I) wherein A represents an adamantylamino group and X has the meaning as defined in claim 1.

4. A platinum complex according claim 1 of the formula (I) wherein A represents a 3,5-dimethyladamantylamino group and X has the meaning as defined in claim 1.

5. A process for the preparation of the platinum complex of the formula (I) according to claim 1 wherein a solution of an alkali metal salt of amminetrihalogenplatinate (II) in a polar organic solvent or in water is reacted with a primary amine of formula R—$NH_2$, wherein R is a tricyclic hydrogen moiety containing 10 to 14 carbon atoms, which may be optionally substituted on the tricyclic ring by one or two alkyl group(s) of 1 to 4 carbon atoms, at a temperature in the range from 0 to 100° C.

6. A process for the preparation of an inclusion complex of the platinum complex of the formula (I) with beta- or gamma-cyclodextrin which may be optionally substituted by a hydroxyalkyl group containing 1 to 6 carbon atoms according to the claim 2, said process being characterized in that a solution of the platinum complex of the formula (I) in an organic solvent is mixed with an aqueous solution of beta- or gamma-cyclodextrin which is optionally substituted by hydroxyalkyl groups containing 1 to 6 carbon atoms, and the solvents are removed as soon as production of the inclusion complex is completed.

7. The platinum complex of the formula (I) or its inclusion complex with beta- or gamma-cyclodextrin according to the claim 1 or 2 for use as a pharmaceutical.

8. A pharmaceutical composition for therapy of oncological diseases characterized in that it contains at least one platinum complex of the formula (I) or its inclusion complex with beta-or gamma-cyclodextrin according to the claim 1 or 2 as the active substance, and at least one pharmaceutical excipient.

* * * * *